United States Patent [19]

Wang et al.

[11] Patent Number: 4,672,101

[45] Date of Patent: Jun. 9, 1987

[54] POLYEPOXY AROMATIC HYDANTOINS

[75] Inventors: Pen-Chung Wang, Midland, Mich.; Chun S. Wang, Lake Jackson, Tex.; Steven P. Crain, Midland, Mich.

[73] Assignee: The Dow Chemical Company, Midland, Mich.

[21] Appl. No.: 773,959

[22] Filed: Sep. 9, 1985

[51] Int. Cl.$^4$ .................. C08G 59/32; C07D 233/30
[52] U.S. Cl. ........................ 528/96; 548/309
[58] Field of Search ............ 548/309; 528/96

[56] References Cited

U.S. PATENT DOCUMENTS

| | | | |
|---|---|---|---|
| 3,449,353 | 6/1969 | Porret et al. | 548/309 |
| 3,631,221 | 12/1971 | Batzer et al. | 528/363 |
| 3,779,949 | 12/1973 | Porret et al. | 528/363 |
| 3,821,243 | 6/1974 | Habermeier et al. | 548/310 |
| 3,907,719 | 9/1975 | Habermeier et al. | 528/363 |
| 3,925,407 | 12/1975 | Stockinger et al. | 548/309 |
| 3,939,175 | 2/1976 | Schmidt et al. | 548/308 |
| 3,975,387 | 8/1976 | Schlicht et al. | 544/162 |
| 3,986,366 | 10/1976 | Dinsmore | 405/172 |
| 4,052,366 | 10/1977 | Habermeier et al. | 528/96 |
| 4,209,608 | 6/1980 | Bateman | 528/363 |
| 4,210,744 | 7/1980 | Bateman | 528/363 |
| 4,281,009 | 7/1981 | Konishi | 548/309 X |
| 4,284,573 | 8/1981 | Arnett et al. | 549/517 |
| 4,340,455 | 7/1982 | Kempter et al. | 528/96 X |
| 4,346,207 | 8/1982 | Maurer et al. | 528/103 |

FOREIGN PATENT DOCUMENTS 784416 8/1977 South Africa .

OTHER PUBLICATIONS

Chemical Abstract, 92:146767b.
Agric. Biol. Chem., 45, pp. 831-838 (1981).
Harvill & Herbst, J. Org. Chem., vol. 19, pp. 21-30 (1944).

Primary Examiner—Earl Nielsen
Attorney, Agent, or Firm—Paul D. Hayhurst

[57] ABSTRACT

A composition comprising a polyepoxy aromatic hydantoin having epoxy functionality on the aromatic and the hydantoin rings.

20 Claims, No Drawings

POLYEPOXY AROMATIC HYDANTOINS

BACKGROUND OF THE INVENTION

The present invention relates to epoxide derivatives of hydantoins having hydroxy aromatic substituents.

Hydantoins having hydroxyphenyl substituents are known. For example, South African Pat. No. 78/4416 teaches the preparation of 5-(p-hydroxyphenyl)hydantoins by reacting phenol with glyoxylic acid or a salt or ester thereof and urea in the presence of an acid catalyst in an aqueous medium. It is taught that the compound is useful as a precursor to p-hydroxyphenylglycine. Similarly, see *Agric. Biol. Chem.*, Vol. 45, p. 831 (1981). Additionally, 5-(p-hydroxyphenyl)hydantoin is known from Harvill and Herbst, *J. Org. Chem.*, Vol. 19, pp. 21-30 (1944), as being prepared by heating p-hydroxybenzaldehyde, potassium cyanide and ammonium carbonate in aqueous alcoholic solution. U.S. Pat. No. 3,939,175 teaches the use of p-hydroxyphenyl hydantoins and related compounds as stabilizers for organic materials such as polymers derived from olefins, vinyl compounds, α,β-unsaturated acids, unsaturated alcohols or amines, epoxides or bisglycidyl ethers, and also for polyphenylene oxides, polyurethanes, polycarbonates, polysulfones, polyamides, polyesters, alkyd resins, and the like.

Dihydroxyphenyl hydantoins also are known. See, e.g., *Chemical Abstracts* 92:146767b and *Chemical Abstracts* 95:62703b.

Polyepoxides of hydantoins and related compounds have been prepared. See, e.g., U.S. Pat. Nos. 3,449,353; 3,631,221; 3,779,949; 3,821,243; 3,907,719; 3,975,387; 3,986,366; 3,925,407; 4,052,366; 4,209,608; 4,210,744; and 4,346,207. When said epoxy compounds are cured, they typically give cured resins having poor thermal stability.

Heretofore, polyepoxy hydantoins having epoxy aromatic substituents have not been disclosed. In view of the deficiencies of known polyepoxy hydantoins, it would be desirable to have an epoxidized hydantoin having improved thermal stability, as indicated by higher glass transition temperatures.

SUMMARY OF THE INVENTION

The present invention is such a class of epoxidized hydantoins of the formula:

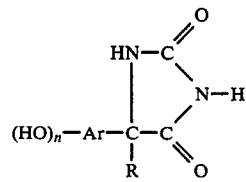

wherein n is at least 1; Ar is an aromatic moiety; R is H, hydrocarbyl, or substituted hydrocarbyl; and Z is a moiety having a terminal epoxide group.

The compounds of the present invention can be employed in the preparation of cured epoxy resins having unexpectedly improved physical properties.

DETAILED DESCRIPTION OF THE INVENTION

The compounds of the present invention are represented generally by the formula:

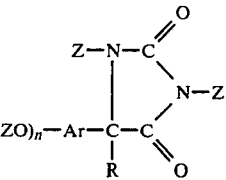

wherein n is at least 1; Ar is an aromatic moiety; R is H, hydrocarbyl, or substituted hydrocarbyl; and Z is a moiety having a terminal epoxide group. Examples of typical R moieties include H, methyl, ethyl, propyl, phenyl, halophenyl, and the like. Preferably, R is H or lower alkyl of up to about 4 carbon atoms, with H and methyl being more preferred.

Examples of typical Ar moieties include phenyl, naphthyl, chlorophenyl, methylene diphenyl, isopropylidene diphenyl, diphenyl and the like. Preferably, Ar has up to 2 aromatic rings, optionally fused. More preferably, Ar is phenyl or substituted phenyl of the formula:

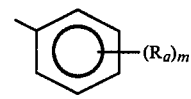

wherein m is from 2 to 5 and each $R_a$ independently is chosen from halogens and the moieties which can be R. The preferred R moieties are the preferred $R_a$ moieties.

Examples of typical Z moieties include alkylenyl oxides such as propylenyl oxide, butylenyl oxide and the like of from about 3 to about 5 carbon atoms, with the preferred Z moiety being

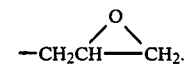

The compounds of the present invention are prepared by contacting a hydroxyaromatic hydantoin with a haloalkylene oxide under reaction conditions.

Examples of the haloalkylene oxides desirably employed in the process include chloropropylene oxide, chlorobutylene oxide, bromopropylene oxide, and the like of up to about 5 carbon atoms, with chloropropylene oxide (epichlorohydrin) being preferred.

The hydroxyaromatic hydantoins are generally known and can be prepared using well-known techniques. See, e.g., U.S. Pat. No. 3,939,175; South African 78/4416; *J. Org. Chem.*, V. 19, pp. 21-30 (1944); 45 *Agric. Biol. Chem.*, 831 (1981). Preferred hydroxy aromatic hydantoins are represented by the formula:

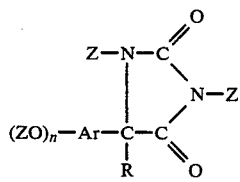

wherein n, Ar and R are as defined hereinabove.

The reaction conditions employed for the addition of haloalkylene oxides to hydroxyl-containing or thiol-containing compounds are well-known. See, e.g., *Hand-* book of Epoxy Resins, by Lee and Neville, McGraw-Hill (1967); and U.S. Pat. No. 4,284,573; the teachings of each of which are incorporated herein by reference. The corresponding reaction between haloalkylene oxides and the nitrogenous hydrogens of hydantoins is also known. See, e.g., U.S. Pat. No. 3,449,353 and 3,631,221; the teachings of each of which are incorporated by reference herein. Said known conditions are advantageously employed in the preparation of the compounds of the present invention. Typically, for example, from about 3 to about 50 moles of haloalkylene oxide are employed per mole of active hydrogen atoms in the hydroxyaromatic hydantoin, with a preferred amount being from about 10 to about 25 moles per mole. Larger or smaller amounts can be employed if desired. The contacting can be performed at any combination of temperature and pressure at which the desired reaction will proceed. Typically, the contacting is performed at elevated temperature. Preferably, the temperature is from about 60° C. to about the boiling point of the haloalkylene oxide. Ambient pressure is preferred for the sake of convenience.

A catalyst is advantageously employed, and can be selected from known catalysts for this reaction, including the wide range of catalysts mentioned in the references cited previously herein. Examples of preferred catalysts include, for example, tetraethylammonium bromide, ethyl triphenyl phosphonium acetate and the like.

The tris- and tetraepoxy resins of the present invention can be cured to form novel epoxy polymers having surprisingly improved properties. The epoxy resins can be cured using well-known techniques. The novel cured resins of the present invention typically are prepared by heating the polyepoxide compound with a curing agent, typically at a temperature of from about 0° C. to about 300° C., preferably from about 25° C. to about 250° C.

As curing agents there can, for example, be mentioned: amines or amides such as aliphatic, cycloaliphatic or aromatic primary, secondary and tertiary amines, for example, monoethanolamine, ethylenediamine, hexamethylenediamine, trimethylhexamethylenediamine, diethylenetriamine, triethylenetetramine, tetraethylenepentamine, N,N-dimethylpropylenediamine-1,3, N,N-diethylpropylenediamine-1,3, bis(4'-amino-3-methylcyclohexyl)methane, 2,2-bis(4'-aminocyclohexyl)propane, 3,5,5-trimethyl-2-(aminoethyl)cyclohexylamine ("isophoronediamine"), N-aminoethylpiperazine, Mannich bases, such as 2,4,6-tris(dimethylaminomethyl)phenol; m-phenylenediamine, p-phenylenediamine, bis(p-aminophenyl)methane, bis(p-aminophenyl)sulfone and m-xylylenediamine; adducts of acrylonitrile or monoepoxides such as ethylene oxide or propylene oxide, to polyalkylenepolyamines such as diethylenetriamine or triethylenetetramine; adducts of polyamines such as excess diethylenetriamine or triethylenetetramine, and polyepoxides such as diomethane polyglycidyl ethers; ketimines, for example, from acetone or methyl ethyl ketone and bis(p-aminophenyl)methane; adducts of monophenols or polyphenols and polyamines; polyamides, especially those from aliphatic polyamines, such as diethylenetriamine or triethylenetetramine and dimerized or trimerized unsaturated fatty acids such as dimerized linseed oil fatty acid ("VERSAMID"); polymeric polysulfides ("THIOKOL"); dicyandiamide; aniline-formaldehyde resins; polyhydric phenols, for example, resorcinol, 2,2-bis(4-hydroxyphenyl)propane or phenol-formaldehyde resins; boron trifluoride and its complexes with organic compounds, such as $BF_2$ ether complexes and $BF_3$ amine complexes, for example, $BF_3$-monoethylamine complex; acetoneacetanilide-$BF_3$ complex; phosphoric acid, triphenylphosphite, polybasic carboxylic acids and their anhydrides, for example, phthalic anhydride, tetrahydrophthalic anhydride, hexahydrophthalic anhydride, 4-methylhexahydrophthalic anhydride, 3,6-endomethylene-tetrahydrophthalic anhydride, methyl-3,6-endomethylene-tetrahydrophthalic anhydride (methylnadicanhydride), 3,4,5,6,7,7-hexachlor-3,6-endomethylene-tetrahydrophthalic anhydride, succinic anhydride, adipic anhydride, azelaic anhydride, sebacic anhydride; pyromellitic dianhydride or mixtures of such anhydrides.

It is particularly advantageous to use curing agents which in themselves yield molding materials of good electrical properties, such as especially cycloaliphatic dicarboxylic acid anhydrides such as, for example, $\Delta^4$-tetrahydrophthalic anhydride or hexahydrophthalic anhydride, or cycloaliphatic polyamines such as, for example, 2,2-bis(4'-aminocyclohexyl)propane or "isophoronediamine".

It is furthermore possible to use cure accelerators, during the cure, and in particular when using polyamides, polymeric polysulfides, dicyandiamide or polycarboxylic acid anhydrides as curing agents; such accelerators are, for example, tertiary amines, their salts or quaternary ammonium compounds, for example, 2,4,6-tris(dimethylaminomethyl)phenol, benzyldimethylamines, 2-ethyl-4-methylimidazole or triamylammonium phenolate; or alkali metal alcoholates such as, for example, sodium hexanetriolate.

The expression "cure" as used here denotes the conversion of the above adducts containing epoxide groups into insoluble and infusible cross-linked products, and in particular as a rule with simultaneous shaping to give shaped articles such as castings, pressings or laminates, or to give two-dimensional structures such as coatings, lacquer films or adhesive bonds.

If desired, it is possible to add active diluents such as, for example, styrene oxide, butylglycidyl ether, isooctylglycidyl ether, phenylglycidyl ether, cresylglycidyl ether or glycidyl esters of synthetic highly branched mainly tertiary aliphatic monocarboxylic acids ("CARDURA E"), or cycloaliphatic monoepoxides such as 3-vinyl-2,4-dioxaspiro(5,5)-9,10-epoxyundecane.

The adducts according to the invention can furthermore be mixed with other curable diepoxide or polyepoxide compounds. As such that can, for example, be mentioned: polyglycidyl ethers of polyhydric alcohols such as 1,4-butanediol, polyethylene glycols, polypropylene glycols or 2,2-bis(4'-hydroxycyclohexyl)propane; polyglycidyl ethers of polyhydric phenols such as 2,2-bis(4'-hydroxyphenyl)propane, 2,2-bis(4'-hydroxy-3',5'-dibromophenyl)propane, bis(4-hydroxyphenyl)sulfone, 1,1,2,2-tetrakis(4-hydroxyphenyl)ethane or condensation products of formaldehyde with phenols produced in an acid medium, such as phenol novolacs or cresol novolacs; polyglycidyl esters of polycarboxylic acids such as, for example, phthalic acid diglycidyl ester, tetrahydrophthalic acid diglycidyl ester or hexahydrophthalic acid diglycidyl ester; triglycidyl isocyanurate, N,N'-diglycidyl-5,5-dimethydantoin, or aminopolyepoxides such as are obtained by dehydrohalogenation of the reaction products of epihalogenohydrin and primary or secondary amines such as aniline or 4,4'-diaminodiphenylmethane; also alicyclic compounds containing several epoxide groups, such as vinylcyclohexene-diepoxide, dicyclopentadienediepoxide, ethylene glycol-bis(3,4-epoxytetrahydrodicyclopentadien-8-yl)ether, (3,4-epoxycyclohexylmethyl)-3,4-epoxycyclohexanecarboxylate, (3′,4′-epoxy-6′-methylcyclohexylmethyl)-3,4-epoxy-6-methylcyclohexanecarboxylate, bis(cyclopentyl)ether diepoxide or 3-(3′,4′-epoxycyclohexyl)-2,4-dioxaspiro-(5,5)9,10-epoxyundecane.

The subject of the present invention therefore also includes curable mixtures which are suitable for the manufacture of shaped articles and which contain the so-called "advanced" adducts containing epoxide groups according to the invention, optionally together with other diepoxide or polyepoxide compounds and also curing agents for epoxide resins such as polyamines or polycarboxylic acid anhydrides.

The compounds of the invention, or their mixtures with other polyepoxide compounds and/or curing agents, can furthermore be mixed, at any stage before cure, with usual modifiers such as extenders, fillers and reinforcing agents, pigments, dyestuffs, organic solvents, plasticizers and the like.

As extenders, reinforcing agents, fillers and pigments which can be employed in the curable mixtures according to the invention there can, for example, be mentioned: coal tar, bitumen, glass fibers, boron fibers, carbon fibers, cellulose, polyethylene powder, polypropylene powder, mica, asbestos, quartz powder, slate powder, aluminum oxide trihydrate, chalk powder, gypsum, antimony trioxide, bentones, silica aerogel ("AEROSIL"), lithopone, barite, titanium dioxide, carbon black, graphite, iron oxide or metal powder such as aluminum powder or iron powder.

The following are, for example, suitable as organic solvents for modifying the curable mixtures: toluene, xylene, n-propanol, butyl acetate, acetone, methyl ethyl ketone, diacetone-alcohol, ethylene glycol monomethyl ether, monoethyl ether and monobutyl ether.

Dibutyl, dioctyl and dinonyl phthalate, tricresyl phosphate, trixylenyl phosphate and also polypropylene glycols can, for example, be employed as plasticizers for modifying the curable mixtures.

Especially for use in the lacquer field, the new adducts containing epoxide groups can furthermore be partially or completely esterified in a known manner with carboxylic acids, such as especially higher unsaturated fatty acids. It is furthermore possible to add other curable synthetic resins, for example, phenoplastics or aminoplastics, to such lacquer resin formulations.

It is furthermore also possible to add other usual additives, for example, flame-proofing agents, agents for conferring thixotropy, flow control agents such as silicones, cellulose acetobutyrate, polyvinyl butyral, waxes, stearates and the like (which are in part also used as mold release agents) to the curable mixtures.

The curable mixtures can be manufactured in the usual manner with the aid of known mixing equipment (stirrers, kneaders, rollers and the like).

The curable epoxide resin mixtures are above all employed in the fields of surface protection, the electrical industry, laminating processes and the building industry. They can be used in a formulation which is in each case suited to the particular end use, in the unfilled or filled state, optionally in the form of solutions or emulsions, as paints, lacquers, sintering powders, compression molding compositions, dipping resins, casting resins, injection molding formulations, impregnating resins and adhesives, as tool resins, laminating resins, sealing and filling compositions, floor covering compositions and binders for mineral aggregates.

A main field of application lies in the field of compression molding powders and of sintering powders. Here the epoxide resin powder mixtures can be processed without pressure or with pressure, according to known processes such as fluidized bed sintering, electrostatic fluidized bed sintering, spraying, electrostatic spraying, compression molding and the like.

SPECIFIC EMBODIMENTS

The following preparations, examples and comparative experiments are intended to illustrate the invention and should not be construed as limiting its scope. All parts and percentages are by weight unless otherwise indicated.

Preparation 1

5-methyl-5′-(p-hydroxyphenyl)hydantoin

One mole (136.2 g) of p-hydroxyacetophenone, one mole (65.1 g) of potassium cyanide, 2 moles (198.4 g) of ammonium carbonate, $(NH_4)_2CO_3$, 300 ml of ethanol and 300 ml of water are placed into a 2-liter round-bottom flask equipped with means for stirring and temperature control. With stirring, the temperature slowly is raised to 50° C.–60° C. and the mixture is held at this temperature for 6 hours. The resulting solution is cooled and is neutralized with concentrated HCl. The resulting slurry is filtered, and the solid is then recrystallized with a 50-volume percent aqueous ethanol solution to give the title compound as a white solid, with a melting point of 244° C., in a yield of 80 percent.

Preparation 2

5-(3,4-dihydroxyphenyl)hydantoin

One mole (148.12 g) of α-methoxyhydantoic acid, 1.25 moles (137.64 g) of catechol, 1 mole (60.06 g) of urea and 300 ml of concentrated HCl (36 percent volume) were placed into the 2-liter flask of Preparation 1, and are stirred at 60° C. to 65° C. for 18 hours. The heterogeneous solution is filtered and is recrystallized from ethanol to give the title compound, with a melting point of 212° C.–214° C., in a yield of 44 percent.

Preparation 3

5-(3,5-dimethyl-p-hydroxyphenyl)hydantoin

To a 3-liter round-bottom flask equipped with a means for stirring and temperature control is added 0.75 mole (112.1 g) of 2,6-dimethyl-p-hydroxybenzaldehyde, 0.75 mole (48.9 g) of potassium cyanide, 250 ml of ethanol, and 300 ml of water. The mixture is stirred for one hour. Then, 2.25 moles (217 g) of ammonium carbonate is added to the mixture and the solution is stirred at 60° C. for 3 hours. The solution is then acidified with concentrated HCl and the product is filtered. The title compound is recovered in a yield of 57 percent, and the structure is verified by proton nuclear magnetic resonance spectroscopy.

Preparation 4

5-(5-bromo-2-hydroxyphenyl)hydantoin

To a 500-ml round-bottom flask equipped with a means for stirring and temperature control is added 0.55 mole (95.16 g) of p-bromophenol, 0.30 mole (44.44 g) of α-methoxyhydantoic acid, and 50 ml of concentrated HCl. The mixture is stirred at 50° C. for 17 hours. The water layer is then decanted, and the gum is washed with water several times. The resulting solid material is then crystallized from an ethanol-water solution to give the title compound having a melting point of 274° C. The structure is confirmed using $C^{13}$ nuclear magnetic resonance spectroscopy.

EXAMPLE 1

1,3-diglycidyl-5-methyl-5'-(p-glycidylphenylether)-hydantoin)

To a 3-liter round-bottom flask equipped with a stirring means, a temperature control means, a dropping funnel and a water separator for circulation-distillation, is added 0.78 mole (160 g) of 5-methyl-5'-(p-hydroxyphenyl)hydantoin, 8.1 g of tetraethylammonium bromide, and 1500 ml of epichlorohydrin. The mixture is stirred for 2 hours at 90° C. The contents of the flask are allowed to cool, and 400 ml of toluene is added. The pressure in the flask is then reduced to 150 mm Hg, and is heated to 70° C.-80° C. Then, 204 g of a 50 weight percent aqueous sodium hydroxide solution is added over a one-hour period with azeotropic removal of the water. Then, distillation is continued for an additional 60 minutes with circulation of epichlorohydrin. The reaction mixture is cooled to 40° C. and sodium chloride is removed by suction filtration. The epichlorohydrin solution is washed with 200 ml of water and is concentrated under reduced pressure to dryness to give an 80–90 percent yield of the title triglycidyl compound. The structure is confirmed using proton nuclear magnetic resonance spectroscopy. Further analysis shows that the product has an epoxy equivalent weight of 130.0 g/equivalent. The viscosity, as measured using a Brookfield viscometer, is 3,760 cps at 60° C. and is 40 cps at 150° C.

EXAMPLE 2

5-((3,4-diglycidylether)phenyl)-1,3-diglycidylhydantoin

To a 3-liter Morton flask is added 0.78 mole (162.2 g) of 5-(3,4-dihydroxyphenyl)hydantoin, 1,450 ml (18.7 moles) of epichlorohydrin, and 8.2 g of tetraethylammonium bromide in 8 ml of water. The resulting mixture is stirred at 90° C. to 110° C. for 2 hours. The solution is then cooled to room temperature and is stirred for an additional 18 hours. Then, 500 ml of toluene is added to the mixture, and 274.6 g of 50 percent aqueous sodium hydroxide is added to the resulting mixture at a temperature of 70° C. to 80° C. and a pressure of approximately 120 mm Hg over a period of 2 hours. The distillation is continued, using a Dean-Stark trap to collect the water generated, until all of the water is removed. The contents of the flask are then filtered, and the filtered material is washed with approximately 200 ml of water. The resulting organic layer is dried over magnesium sulfate, is filtered, and is stripped of the solvents to give a 60 percent yield of the title compound having an epoxy equivalent weight of 156.3±0.5 g/equivalent. The structure is confirmed using proton nuclear magnetic resonance spectroscopy.

EXAMPLE 3

The trisepoxide of Example 1, N,N'-diglycidyl-5-methyl-5-(p-glycidylphenylether)hydantoin, is cured. The trisepoxide is produced according to the method of Example 1, and has an epoxy equivalent weight of 131. A 144.2-g sample of the trisepoxide is preheated to 100° C. Then, 62.0 g (90 percent of the theoretical molar amount needed) of bis(4-aminophenyl)sulfone is added with stirring. The sulfone is added all at once. When the solids dissolve, the material is placed under a vacuum to degas. The degassed material is then poured into two preheated molds having temperatures of 125° C., and is allowed to gel. The molds are then placed into an oven at 150° C. for one hour, 200° C. for one hour, and 250° C. for one hour. The properties of the cured material are found in Table I.

EXAMPLE 4

The procedure of Example 3 is repeated with the following exceptions: the curing agent is methylene dianiline; after gelling, the molds are placed into an oven at 125° C. for 2 hours, 175° C. for 2 hours, and 225° C. for 2 hours. The properties of the resulting cured material are found in Table I.

EXAMPLE 5

Three grams of the tetraepoxy resin of Example 2 and 1.26 g of bis(4-aminophenyl)sulfone are mixed into a tin cup and gelled at 177° C. The cup is then placed into an oven at 150° C. for 2 hours, 200° C. for 2 hours, and 225° C. for 2 hours. The properties of the cured material are summarized in Table I.

EXAMPLES 6 AND 7

The procedure of Example 3 is repeated except that the hydantoin-based starting materials are, respectively, N,N'-diglycidyl-5-(p-glydicylphenylether)hydantoin and N,N'-diglycidyl-5-(3,5-dimethyl-4-glycidyletherphenyl)hydantoin. The physical properties of the cured materials are found in Table I.

Comparative Experiment 1—(not an embodiment of the present invention)

The procedure of Example 3 is repeated except that the epoxy resin employed is tris(4-glycidyletherphenyl)methane which has a viscosity of about 17,000 cps at 60° C. The physical properties of the cured material are summarized in Table I.

TABLE I

| Run | $G_{IC}{}^2$ (KJ/m²) | HDT[2] (°C.) | Tg (°C.) | Izod Impact (ft lb/in) | Tensile (PSI) | % Elongation | Onset of Decomp (°C.) | Young Modulus (PSI) | Coef[3] | Gel Time (min) |
|---|---|---|---|---|---|---|---|---|---|---|
| C.E. 1 | 0.08 | >240 | 320 | 0.00 | 8 × 10³ | 1.6–1.9 | 350 | 5 × 10⁵ | 6.23 | 9 |
| Ex. 3 | 0.18 | >240 | 257 | 0.26 | 4.4 × 10³ | 1.6 | 340 | 5 × 10⁵ | 4.5 | 6 |
| Ex. 4 | — | — | >240 | 0.25 | 6.2 × 10³ | 1.66 | — | 5.4 × 10⁵ | 5.9 | 6 |
| Ex. 5 | — | — | >250 | — | — | — | ~270 | — | — | 1.9 |
| Ex. 6 | 0.12 | >240 | >240 | 0.25 | 4.8 × 10³ | 1.3 | 2% @ 300 | 4.6 × 10⁵ | 4.87 | 6 |

TABLE I-continued

| | Property Comparisons[1] | | | | | | | | |
|---|---|---|---|---|---|---|---|---|---|
| Run | $G_{IC_2}$ (KJ/m$^2$) | HDT[2] (°C.) | Tg (°C.) | Izod Impact (ft lb/in) | Tensile (PSI) | % Elon- gation | Onset of Decomp (°C.) | Young Modulus (PSI) | Coef[3] | Gel Time (min) |
| Ex. 7 | 0.17 | >240 | >240 | — | 6.5 × 10$^3$ | — | — | — | — | — |

[1] 95% Stoichiometric cured with diaminodiphenylsulfone: 2 hours @ 150° C., 2 hours @ 200° C., 1 hour @ 250° C.
[2] Heat distortion temperature
[3] Coefficient of Thermal Expansion (× 10$^{-5}$ deg$^{-1}$ C.)

What is claimed is:

1. A composition comprising a compound of the formula:

$$Z-N-C(=O)-N-Z$$
$$(ZO)_n-Ar-C(R)-C(=O)$$

wherein n is at least 1; Ar is an aromatic moiety; R is H, hydrocarbyl, or substituted hydrocarbyl; and Z is a moiety having a terminal epoxide group.

2. A composition of claim 1 wherein Z is $$-CH_2-CH(-O-)CH_2.$$

3. A composition of claim 2 wherein n is 1 or 2.
4. A composition of claim 3 wherein n is 1.
5. A composition of claim 3 wherein n is 2.
6. A composition of claim 3 wherein R is H or lower alkyl of up to about 4 carbon atoms.
7. A composition comprising an adduct of:
   (a) a composition of claim 1;
   (b) a curing agent for epoxy resins; and, optionally,
   (c) a curing catalyst.
8. A composition of claim 7 wherein component (a) is a composition of claim 2.
9. A composition of claim 7 wherein component (a) is a composition of claim 3.
10. A composition of claim 7 wherein component (a) is a composition of claim 4.
11. A composition of claim 7 wherein component (a) is a composition of claim 5.
12. A composition of claim 6 wherein R is methyl or H.
13. A composition of claim 1 wherein Ar is aryl of up to 2 rings.
14. A composition of claim 13 wherein Ar is phenyl or substituted phenyl.
15. A composition comprising a compound of the formula $$(R_a)_m-\text{phenyl}(OZ)_n-C(R)-C(=O)-N(Z)-C(=O)-N-Z$$

wherein Z is $$-CH_2-CH(-O-)CH_2,$$

n is 1 or 2, R is H or alkyl of up to about 4 carbon atoms, m is from zero up to (5−n), and each $R_a$ independently is H or alkyl of up to 4 carbon atoms.

16. A composition of claim 15 wherein R is H or methyl, and n is 1.
17. A composition of claim 16 wherein the —OZ moiety is para to the phenyl-hydantoin bond.
18. A composition of claim 15 wherein n is 2.
19. A composition of claim 18 wherein $R_a$ is H.
20. A composition comprising an adduct of a composition of claim 15, a curing agent for epoxy resins, and optionally a curing catalyst.

* * * * *

UNITED STATES PATENT AND TRADEMARK OFFICE
CERTIFICATE OF CORRECTION

PATENT NO. : 4,672,101

DATED : June 9, 1987

INVENTOR(S) : Pen-Chung Wang; Chun S. Wang; and Steven P. Crain

It is certified that error appears in the above-identified patent and that said Letters Patent is hereby corrected as shown below:

Col. 3, lines 47-48, delete "2-(aminoethyl)" and insert
-- 3-(aminomethyl) --.

Col. 4, line 14, delete "sebacic anhydride;" and insert
-- sebacic anhydride, maleic anhydride, dodecenyl-succinic anhydride; --.

Signed and Sealed this

Twenty-second Day of March, 1988

Attest:

DONALD J. QUIGG

Attesting Officer

Commissioner of Patents and Trademarks